United States Patent [19]

Chang

[11] Patent Number: 5,256,542
[45] Date of Patent: * Oct. 26, 1993

[54] SELECTING LOW FREQUENCY ANTIGEN-SPECIFIC SINGLE B LYMPHOCYTES WITH CORRECTION FOR BACKGROUND NOISE

[75] Inventor: Tse W. Chang, Houston, Tex.

[73] Assignee: Tanox Biosystems, Inc., Houston, Tex.

[*] Notice: The portion of the term of this patent subsequent to May 25, 2010 has been disclaimed.

[21] Appl. No.: 905,040

[22] Filed: Jun. 26, 1992

Related U.S. Application Data

[63] Continuation-in-part of Ser. No. 848,249, Mar. 9, 1992.

[51] Int. Cl.$^5$ .................... G01N 21/64; G01N 33/58; G01N 33/536
[52] U.S. Cl. .................... 435/7.24; 435/962; 436/536; 436/546; 436/172
[58] Field of Search .................... 435/7.24, 808, 962; 436/536, 546, 63, 172, 800, 805

[56] References Cited

U.S. PATENT DOCUMENTS

| | | | |
|---|---|---|---|
| 4,510,244 | 4/1985 | Parks et al. | 435/172.2 |
| 4,727,023 | 2/1988 | Wang et al. | 435/7 |
| 4,918,000 | 4/1990 | Schubert | 435/7 |

OTHER PUBLICATIONS

Ault, K. A. "Flow Cytometric Evaluation of Normal and Neoplastic B Cells" in *Manual of Clinical Laboratory Immunology* 3rd ed N. R. Rose ed 1986 American Society for Microbiology, Washington, D.C. pp. 247–253.

*Primary Examiner*—Esther L. Kepplinger
*Assistant Examiner*—Nancy J. Parsons
*Attorney, Agent, or Firm*—Eric P. Mirabel

[57] ABSTRACT

Disclosed are immunofluorescence staining methods which increase the likelihood that antibodies expressed by a single B cell selected and sorted by fluorescence activated cell sorting are specific for the antigen of interest, and which also allow selection of B cells expressing antibodies of high affinity for the antigen of interest. The antigen-specific single B cells are to be used in a procedure which amplifies and selects their $V_H$ and $V_L$ sequences. The selection for B cells expressing antibodies to specific antigens is increased by labeling B cells with at least two antigen probes, where each antigen probe includes the antigen of interest and the difference between the two probes is that each is labeled with a different fluorochrome. The positive selection achieved using antigen probes with two different colors is preferably combined with a negative selection step, in which autofluorescent cells and sticky cells exhibiting fluorescence for the third irrelevant surface marker are excluded out. The specificity of sorting of the desired B cells can be further enhanced by staining those antigen-specific B cells which produce the immunoglobulin isotype (typically IgG), with targeting molecules reactive with a B cell marker, such as γ chain and CD19, that are conjugated with a different fluorochrome. Thus, the antigen-specific IgG-producing B cells of interest may be labeled with these unique reagents in four color FACS (including one for negative selection), which can sort the desired antigen-specific B cells at enhanced proportions. The differences in relative intensities between the antigen labels and the isotype labels (e.g., IgG labels) among the different antibodies of the single cells selected can be used to determine the relative antigen binding affinity of those antibodies. For example, the ratio of antigen label to IgG label can be calculated for each labeled B cell. The higher the ratio, the higher the relative affinity of the antibodies on the B cells for the antigen. After sorting the B cells with FACS, those B cells with high affinity are preferred for analysis by the single cell-PCR procedure to amplify and clone the $V_H$ and $V_L$ segments of interest.

15 Claims, No Drawings

SELECTING LOW FREQUENCY ANTIGEN-SPECIFIC SINGLE B LYMPHOCYTES WITH CORRECTION FOR BACKGROUND NOISE

This application is a continuation-in-part of co-pending application Ser. No. 07/848,249, filed Mar. 9, 1992.

FIELD OF THE INVENTION

The invention relates to the use of a unique cell staining methodology in conjunction with multiple-color fluorescence-activated cell sorting to identify and isolate low-frequency B cells which express monoclonal antibodies with a particular antigen binding specificity and, preferably, a high affinity, for the purpose of amplifying the $V_H$ and $V_L$ sequences in those individual B cells.

BACKGROUND OF THE INVENTION

B cells produce antibodies, and each B cell produces an antibody having one particular antigen specificity (i.e., the antibody is monospecific). If one expands a single B cell clone, the antibodies produced by the expanded population of B cells are homogeneous. Hybridoma technology, which has been in existence since 1975, enables one to immortalize individual B cells, and thereby allows one to expand a population of individual B cell clones to obtain sufficient antibodies so that the immortalized population can be screened to isolate those B cells producing antibodies having a particular antigen specificity. The B cell hybrids of interest can be grown in a large scale to make large quantities of homogeneous monoclonal antibodies, which are useful for diagnostic and therapeutic purposes. Kennett, R. H., et al, *Monoclonal Antibodies* (Plenum Press, New York 1980); Borrebaeck, C. A. K. and Larrick, J. W., *Therapeutic Monoclonal Antibodies* (Stockton Press, New York 1990); Winter, G. and Milstein, C. *Nature* 349:293 (1991).

Hybridoma technology generally works best for preparing purely murine monoclonal antibodies. Hybrids made from fusing human B cells with human or murine myeloma cells are generally unstable, and tend to lose the human chromosomes and the ability to produce antibodies. Transforming human B cells with the Epstein-Barr virus (EBV) offers an alternative way to immortalize them. However, the transformation frequency is relatively low and the transformants are also not stable and often lose antibody-producing ability.

An alternative method, often referred to as the "combinational V region library" method, has been developed to identify and isolate antibody fragments having a particular antigen specificity. Sastry, L. et al., *Proc. Natl. Acad. Sci. U.S.A.* 86:5728 (1989); Huse, W. D. et al., *Science* 246:1275 (1989); Orlandi, R. et al., *Proc. Natl. Acad. Sci. U.S.A.* 86:3833 (1989). This technique relies on polymerase chain reaction (PCR) techniques. Using degenerate oligonucleotide 5'-end primers corresponding to the leader peptides or the N-terminal framework segments of $V_H$, $V_\kappa$, and $V_\lambda$, and 3'-end primers corresponding to the CH1 domain of a heavy chain such as $\gamma$ and to the constant regions of light chains $\kappa$ and $\lambda$, the $V_H$, $V_{78}$, and $V_{80}$, regions of a population of B cells are amplified with PCR. The pools of these $V_H$, $V_{78}$, and $V_{80}$, genes are referred to as $V_H$, $V_\kappa$, and $V_{80}$, libraries of a particular B cell population. Using specially designed vectors derived from a bacteriophage, a $V_H$ segment and a $V_L$ segment can be inserted into the vector and coexpressed in an *E. coli* bacterial host cell. The random combination of the $V_H$ and $V_L$ libraries creates an extremely large $VI_H$-$VI_L$ combinatorial library. Each pair of combined $V_H$ and $V_L$ forms a unique antibody Fv fragment with a particular antigen-binding specificity.

The recombinant $\lambda$ phage including the expression vectors that contain the combined $V_H$ and $V_L$ genes can be cloned, and then various methods can be applied to determine the antigen-reactivity of the antibodies which are expressed. In one earlier expression system, the combined $V_H$ and $V_L$ gene segments in bacteriophage $\lambda$ were expressed as soluble Fab fragments in *E. coli*. In a more recently developed system, the combined $V_H$ and $V_L$ fragments are expressed as a part of a protein on the surface of a filamentous bacteriophage, designated fd. In this latter system, the bacteriophage expressing the antibody fragment of interest can be isolated using affinity chromatography. McCafferty, J. *Nature* 348:552 (1990).

When using EBV transformation or cell fusion as described above to obtain monoclonal antibodies of particular specificity, a number of factors determine the probability of isolating the desired antibodies. Some of these factors are:

1. The pre-fusion number of B cells expressing the desired antibodies in the B cell population (referred to as the frequency of desired B cells);
2. The number of B cells in the B cell population which are fused with myelomas or transformed by EBV (respectively referred to as the frequency of fusion or transformation);
3. The stability of the immortalized cells.

Referring to factor "1" above, the frequency of desired B cells in mice is affected by whether the mice from which the B cells are derived are unexposed, immunized, or hyperimmunized with the antigen. By some estimates, the antibody repertoire in a mouse could represent over $10^{10}$ different antibody species. However, at any given time, there may be only $10^7$–$10^8$ B cell clones in a particular mouse. Winter, G. and Milstein, C. *Nature* 349:293 (1991). This suggests that for most antigenic epitopes, the frequency of B cells producing reactive antibodies may be in the order of $1 \times 10^{-5}$ or $1 \times 10^6$, or less. It is also known that in a hyperimmunized mouse, the frequency of B cells specific for the immunogen may account for several percent of the total, or more.

When making human monoclonal antibodies, the frequency of desired B cells is affected by whether the human donors from whom the B cells are derived are immunized with the antigen through infection, vaccination, or other exposure. Depending on the intensity of a viral infection, the stage in the immune response, and the immunogenicity of the particular viral antigen, the frequency of B cells in the infected person specific for a particular antigenic epitope on a viral protein may range from $1 \times 10^{-3}$ to $1 \times 10^{-5}$ for the more dominant epitopes and less than $1 \times 10^{-5}$ for the relatively silent epitopes. The frequency of IgG-expressing B cells specific for a protein allergen will often vary among different individuals, and may vary with the concentration of the allergen in the environment. The frequencies of B cells specific for autologous antigens, such as IgG, platelet surface antigens, leukocyte surface antigens, nuclear proteins, or DNA, will also vary among different individuals. For a relatively nonimmunogenic antigenic epitope on a large protein molecule, such as the CD4 binding site on gp120 of HIV-1, the B cells expressing antibodies specific for an antigenic epitope thereof in a moderately immunized mouse or an HIV-1 infected person may only occur at a frequency of $1 \times 10^{-5}$ or lower among the IgG-bearing B cells. For an antigen the B cell donor has not been exposed to, the frequency of B cells specific for the antigen may be $1 \times 10^6$ or lower.

In a fusion procedure for preparing murine hybridomas, immunized mouse spleen cells are fused with myeloma cells. The number of lymphocytes in a mouse spleen is about $1 \times 10^8$. B cells account for about 10% of the total, and among B cells, IgG-expressing B cells account for about 20%. Thus, in a mouse spleen, there are about $2 \times 10^6$ IgG-expressing B cells.

In performing a cell fusion or EBV transformation procedure to immortalize IgG-expressing B cells from a person, one may typically take 100 ml peripheral blood from the donor. There are about $1 \times 10^8$ lymphocytes in this amount of blood. Among them, B cells account for about $1-1.5 \times 10^7$, and IgG-expressing B cells account for about $2-3 \times 10^6$.

If the targets of immortalization are antigen-specific IgG-expressing B cells occurring at moderately low frequency, for example, $1 \times 10^{-5}$ among the IgG-bearing B cells, there will only be about 20-30 such B cells in a mouse spleen or in 100 ml of peripheral human blood.

The difficulty which stems from having such a small number of B cells producing the desired antibody relates to factor "2" above: the frequency of cell fusion or transformation. A skillful technician using a good fusion protocol can generate about 10,000 hybrids from the approximately $1 \times 10^7$ B cells which are taken from the spleen of a mouse. This corresponds to a fusion frequency of 1 in 1000 B cells. The cell fusion and EBV-transformation frequencies for human B cells are at least about 1 to 2 orders of magnitude lower. Thus, if one is starting with only about 20-30 B cells with the desired antigenic specificity, the chances of immortalizing one of the desired B cells is very slim.

Factor "3" above refers to the stability of the immortalized cells. As noted above, while murine hybridomas are generally stable, human hybridomas and EBV transformants are much less stable. Sequential subcloning is usually required to obtain stable human hybrids and transformants. However, even with such subcloning, which can be a laborious procedure, stable antibody-secreting cell lines cannot be obtained for a large portion of human hybrids and transformants.

While the combinatorial library methodology can be used to produce antigen-specific antibody fragments in bacterial host cells, it also suffers certain drawbacks related to the low frequency of antigen-specific B cells. For determining whether a particular B cell expresses antibody molecules of desired antigen-binding specificity, the $V_H$ and $V_L$ segments of the mRNAs of the heavy and light chains need to be reverse transcribed into cDNA, amplified by PCR, and the resulting gene segments must be cloned, sequenced, and incorporated into expression vectors. The two gene segments must then be coexpressed in a mammalian cell or other system, and the fragments produced must be characterized for antigen-binding specificity and for relative binding affinity. In a natural immune response, the B cells expressing the antibodies specific for an antigen expand, resulting in higher representations of such cells among the B cell repertoire. The combination of the desired $V_H$ and $V_L$ gene segments are expressed only by the antigen specific B cells. The combinatorial library methodology separates the $V_H$ and $V_L$ genes and recombines them in a random fashion. If B cells secreting an antibody of desired antigen-binding specificity are present at a frequency of $1 \times 10^{-5}$, the combinatorial library will expand the $V_H$-$V_L$ library. Depending on the diversity of the repertoire in the $V_H$ and $V_L$ libraries, the original $V_H$ and $V_L$ combination will be present at a frequency of probably about $1 \times 10^{-10}$. It has been suggested that certain $V_H$-$V_L$ combinations resulting from this genetic manipulation may also have the desired antigen specificity. However, this possibility is yet to be substantiated by experimentation. Winter, G. & Milstein, C. *Nature* 349:293 (1991).

Screening large numbers of bacteriophage particles expressing the desired fragment is generally more efficient than screening hybridomas or EBV transformants for the corresponding antibody. The typical screening methods for bacteriophage plaques can handle up to $10^6$ or $10^7$ phages, assuming that the availability of antigen suitable for the antigen-binding assays is not a limiting factor. However, for certain soluble antigens or antigenic epitopes, screening bacteriophages incorporating the reactive antibodies is difficult, because the antigens are limited or only available in soluble form. Additionally, for certain other antigens including membrane-bound proteins, the conformational epitopes on the antigens are altered if the antigens are solubilized from the membrane, and they will not react with the fragments being screened.

Additionally, if one is screening the antibody-expressing bacteriophages on an immunoblotting plate, about 50,000 plaques can be screened on one plate. In an extremely ambitious experiment, 100 plates may be screened. This screens about $5 \times 10^6$ plaques or phages, which is much below the theoretical number of plaques which need to be screened to obtain the desired fragment.

A new method has been described for expressing the antibody fragment $V_H$-$V_L$ as a part of a protein on the surface of filamentous phage. It has been claimed that the phage expressing the specific antibody can be affinity purified from a large number of phages using an antigen-conjugated affinity column. McCafferty, J. et al., *Nature* 348:552 (1990). Theoretically this sounds plausible, however, it is yet to be proven that the methodology can identify and purify one specific phage from $1 \times 10^{10}$ phages. In addition, one major problem in immunoblotting and affinity chromatography methods is that antibodies with a moderate affinity for the antigen will be selected. This allows the inclusion of many cross-reactive or sticky antibodies, causing burdens in the sequential screening procedures.

Various methods have been employed to enrich the desired B cells when they occur at low frequency. These methods can be used to enrich the desired B cells whether one is attempting to isolate the $V$, and $V_L$ fragments by hybridoma fusion technology, EBV transformation, or the combinatorial library methodology. These enrichment methods include fluorescence-activated cell sorting (FACS), panning against antigen-coated plastic surface, binding to antigen-coated magnetic beads, or resetting with antigen-coated red blood cells.

These procedures for enriching antigen-specific B cells, however, all suffer from a certain degree of non-specificity. For example, panning or absorbing to plates or beads yields from about one to several percent of nonspecific binding. Rosetting of cells by antigen-coated red blood cells also has about the same degree of nonspecific activity. For cell sorting using FACS, the nonspecific sorting will depend on the stringency of the gate setting, but it usually ranges from 0.1 to several percent depending on the nature of the antigen.

An additional problem in a typical FACS procedure where mixed leukocytes are screened is background noise. An FACS apparatus operates by having a number of channels, which can each view a different fluorochrome. Single cells can be selected based on their fluorescence, or lack of fluorescence. Background noise in an FACS apparatus arises primarily from two sources. One source of noise is exhibited by certain activated cells or proliferating cells of various leukocyte subpopulations that contain high concentrations of certain metabolites, which cause these cells to exhibit autofluorescence even in the absence of fluorochrome labeling. Another possible source of background noise arises because some of the activated cells, and some monocytes and macrophages, possess sticky cellular plasmamembranes. Fluorescent probes will non-specifically adhere to the sticky plasmamembrane and create an additional source of background fluorescence in the cell sample.

Assuming that the B cells expressing antibodies having the desired antigen-binding properties in a human donor occur at a frequency of about $10^{-5}$ to $10^{-6}$ (which is a reasonable estimate for B cells specific for a weak antigenic epitope in an individual with exposure to the antigen or an individual naive to the antigen) the B cell enrichment procedures discussed above are not useful. If an enrichment method provides 1% nonspecific activity, then the desired B cells will average only about one in 1000 or 10,000 B cells isolated. Obviously, the single cell-PCR procedure to be described below for identifying and isolating antibodies of desired antigen-binding specificity would not work at such a low frequency. Thus, a method to increase the proportion of antigen-specific B cells among the single B cells selected for performing the single cell procedure is needed.

SUMMARY OF THE INVENTION

The invention includes methods that increase the likelihood that antibodies expressed by a single B cell selected by a fluorescence-sorting technique, FACS, are specific for the antigen of interest, and that also allow selection of B cells expressing antibodies of high affinity for the antigen of interest. The sorting for B cells expressing antibodies to specific antigens is increased by labeling B cells with at least two antigen probes, where each antigen probe includes the antigen of interest and the difference between the two probes is that each is labeled with a different fluorochrome, F1 and F2, respectively. Preferably, the sorting of desired B cells is also increased by excluding autofluorescent cells that exhibit fluorescence at greater than a specified level, and by excluding sticky cells of various leukocyte subpopulations that exhibit fluorescence for fluorochrome F3, when the mixture of cells are treated with F3 conjugated to a probe specific for an irrelevant cell type, such as a monoclonal antibody a T cell surface antigen. The positive selection using two antigen probes will exclude those B cells expressing antibodies specific for either of the fluorochromes. The negative selection achieved by gating out all cells exhibiting fluorescence at greater a specified level, or fluorescence to fluorochrome F3, will exclude not only cells expressing the marker the probe is specific for, but also those cells, including B cells, which do not express such a marker but are autofluorescent or possess sticky membranes that any of the fluorescent probes adhere to nonspecifically.

Also, to further increase the specificity of the selected B cells, it is preferred if, when cross-linkers or carrier molecules are employed in the conjugation of antigen to fluorochrome, different cross-linkers and carrier molecules are used for each of the two antigen probes.

The specificity of sorting of the desired B cells can be further enhanced by labeling those B cells which produce the immunoglobulin isotype (typically IgG) of interest. The surface antigens suitable for labeling are the $\gamma$ chain, $\kappa$ Or $\lambda$ chains, CD19, Ia, and the Fc receptors. This labeling of antigens on the B cells is preferably done with one targeting molecule, associated with fluorochrome F4. For example, affinity-purified IgG-F(ab')$_2$ of goat-anti-human IgG ($\gamma$ chain) or affinity purified IgG-F(ab')$_2$ of rabbit-anti-human CD19 may be used as the specific probe for the targeted B cell population. Thus, the antigen-specific IgG-producing B cells of interest may be labeled with these unique reagents in three or preferably four-color FACS (one color for negative selection), which can sort enhanced proportions of the desired antigen-specific B cells by a combination of positive-selection and negative-selection gatings.

The differences in relative intensities between the antigen labels and the isotype labels (e.g., IgG labels) among the different antibodies of the single cells selected can be used to determine the relative antigen binding affinity of those antibodies. For example, the ratio of antigen probe label to IgG label (e.g., the fluorescence intensity F1/F4) can be calculated for each labeled B cell. The higher the ratio, the higher affinity the antibodies on the B cells have for the antigen. After sorting the individual antigen-specific B cells with FACS into separate containers, such as wells of $8 \times 12$ (96 well) microculture plates, those B cells with high F1/F4 ratios are preferred for analysis by the single cell-PCR procedure to amplify and clone the $V_H$ and $V_L$ segments of interest. This selection technique can result in $V_H/V_L$ fragments which are highly specific for the antigen of interest.

It is preferred that antigen-specific antibodies on B cells with frequencies of about $10^{-5}$ or lower are labeled in the manner described, because B cells expressing antibodies binding to the carrier proteins, fluorochromes, or cross-linkers may have comparable or even higher frequencies. Accordingly, unless one is using the labeling system of the invention, B cells and other cells with sticky membranes or which autofluoresce, and B cells binding to carrier proteins, fluorochromes, or cross-linkers may become labeled along with those which express antibodies to the desired antigen, and those cells will get sorted and selected along with those expressing antibodies to the desired antigen.

DETAILED DESCRIPTION OF THE INVENTION

A.

Rationale of selecting and isolating low-frequency antigen-specific B cells for single cell PCR For immortalizing antigen-specific B cells that occur at lower than $1 \times 10^{-5}$ in frequency and in fewer than 1000 cells in a sample, the existing hybridoma methods, EBV-transformation methods, and combinatorial V region library methods are deficient. The methods of the present invention are designed to select and isolate the antigen-specific B cells of interest preferably for use in $V_H$ and $V_L$ PCR analyses and production of antibody fragments.

The present invention relies on two techniques which have both been established for working with single cells. One technique incorporates a special accessory which can be used in FACS to deflect single cells into separate containers. Both FACS Star Plus ™ from Becton Dickinson (Foster City, CA) and Epics C from Coulter Epics Division (Hialeah, FL) have outfitted cloning accessory apparatus which can be programmed to dispense single particles or cells into selected compartments of a standard 96 well microtiter culture plate. This kind of cell sorting accessory has been employed to subclone hybridoma cells which secrete high amounts of immunoglobulins. Marder, P. et al., *Cytometry* 11:498 (1990).

The other technique relied on is that PCR can be performed on single B cells to amplify the $V_H$ and $V_L$ segments. Larrick, J. W. et al., *Bio/Technology* 7:934(1989). Numerous studies have indicated that degenerate oligonucleotides can be prepared to serve as the 5'-end primers for $V_H$ and $V_\epsilon$ or $V_\lambda$. The combinatorial library method of making targeting molecules relies on such primers. Furthermore, numerous experiments have shown that PCR can amplify the gene segments of interest, such as $V_H$ and $V_L$, from a single cell. Because of the ability to work with even a single cell, the PCR approach is preferred in the present invention for producing targeting molecules where the B cells of interest occur at low frequency.

Oligonucleotides suitable for use as the 5'-end primers for human $V_H$ and $V_\epsilon$ have been shown to amplify these segments almost 100% of the time in single cells taken from the human lymphoblastoid IgG cell lines. The preferred set of 5'-end primers for $V_H$ consists of 5 degenerate groups of oligonucleotides and one nondegenerate oligonucleotide (SEQ ID NOS: 1-6), totaling 53 sequences. This set of primers corresponds to the first 5 amino acids of the mature immunoglobulins, and covers the known sequences of the 155 human $V_H$ segments which have been sequenced.

Referring to SEQ ID NO:1, several other oligonucleotides based on it are also within the set of 5'-end primers for human $V_H$. These other oligonucleotides are variations on SEQ ID NOS:1-2 and SEQ ID NOS:4-6. The variations in SEQ ID NO:1 which yield these other oligonucleotides is that the first Guanidine nucleotide can be a Cytosine, the sixth Guanidine can be a Thymidine, and the thirteenth Guanidine can be a Thymidine.

The variations in SEQ ID NO:2 which yield these other oligonucleotides are that the fourth, eighth and ninth Adenosines can be a Guanidines. The variations in SEQ ID NO:4 which yield these other oligonucleotides are that the sixth Guanidine can be an Adenosine or a Cytosine, and the ninth and twelfth Adenosines can be Guanidines. The variations in SEQ ID NO:5 which yield these other oligonucleotides are that the fourth Adenosine can be a Guanidine, the eighth Adenosine can be a Cytidine, and the twelfth Adenosine can be a Guanidine. The variations in SEQ ID NO:5 which yield these other oligonucleotides are that the fourth Guanidine can be a Thymidine, the tenth Cytidine can be a Thymidine, and the fourteenth Cytidine can be a Guanidine. The variations in SEQ ID NO:5 which yield these other oligonucleotides are that the fourth Guanidine can be a Thymidine, the tenth Cytidine can be a Thymidine, and the fourteenth Cytidine can be Guanidine. These variations in SEQ ID NOS: 1-2 and 4-6 will yield the 53 different oligonucleotides which constitute the set of 5'-end primers for $V_H$.

The preferred set of 5'-end $V_\kappa$ primers consist of 2 degenerate groups (SEQ ID NOS:9 and 12) and 4 nondegenerate oligonucleotides (SEQ ID NOS:7-8 and 10-11), totaling 10 sequences. The variations in SEQ ID NO:9 which yield other oligonucleotides are that the third Cytidine can be a Thymidine, and the sixth Cytidine can be a Thymidine. The variations in SEQ ID NO:12 which yield other oligonucleotides are that the seventh Cytidine can be a Guanidine.

The procedure we have employed to amplify the $V_H$ and $V_L$ sequences from single B cells is a "semi-nested PCR" methodology. The procedure calls for two round of PCR amplification. The same sets of degenerate 5' $V_H$ and $V_K$ primers are used for both rounds of PCR, whereas the 3' primers used in the second round of PCR are derived from the internal region toward the 3'-end of the DNA fragments amplified in the first round of PCR. Thus, in the second round of PCR, the 5' end is not nested, while the 3'-end can be considered nested. The procedure is hence a semi-nested PCR. The 3' primers that have been used successfully in our laboratory for $V_H$ and $V_L$ amplification are SEQ ID NO:13 (corresponding to amino acid residue numbers 136-148), SEQ ID NO:14 (corresponding to amino acid residue numbers 122-127), SEQ ID NO:15 (corresponding to amino acid residue numbers 125-135), and SEQ ID NO:16 (corresponding to amino acid residue numbers 117-125).

The most appropriate number of reaction cycle in each round of PCR is 20 cycles for first round and 40 cycles for second round of PCR. The procedure has been shown to be applicable in ARH-77, VA165, VA200, and 4.8D cells. In each case, only ⅛ of cDNA synthesized from the RNA prepared from a single cell by RNA-zol ™ extraction is required for amplification of either $V_H$ or $V_K$ sequence.

The $V_H$ and $V_L$ gene segments obtained by PCR amplification can be cloned and sequenced by incorporating them into an appropriate expression vector. For speedily screening the antibody fragments for antigen binding properties, a transient host cell expression system is preferably employed. Supernatants taken from the transiently expressing host cells can be used to assay the antigen-binding specificity of the $V_H/V_L$ fragments, and their relative affinity for the antigen of interest.

B.

Methods for selecting and isolating low-frequency antigen-specific B cells

When the target B cell occur at a frequency of $1 \times 10^{-5}$ or lower among the IgG-expressing B cells, and if one starts with purified IgG-bearing B cells and if the method of selection has 1% non-specific selection, the specific B cells among those selected will account for fewer than 1 out of 1000. Such a low frequency of specific B cells is not practical for conducting single cell-PCR, as too few antigen-specific B cells are present in the selected single B cells than can be processed, as a practical matter, by the single cell PCR procedure.

In the single cell PCR procedure, the $V_H$ and $V_L$ gene segments of each of the single B cells selected are to be amplified, cloned, sequenced, co-expressed, and the antibody fragments characterized. Because of the time required for analyzing each of the individual B cells, a single cell PCR experiment can screen only about 10–20 B cells. Thus, when using PCR to isolate the gene expressing an antibody fragment from single B cells, the B cells expressing the antibody of interest should preferably account for 10% or more of the total number of B cells processed. This means that the non-specific B cells included in the selection procedure must be in the order of about $1 \times 10^{-4}$ to (0.01%) or lower, so that the antigen-specific B cells account for about 1 out of 10 B cells selected and processed. This low level of non-specificity can be achieved by the cell sorting methods of the present invention.

Certain models of fluorescence-activated cell sorters, such as the FACS Star Plus TM of the Becton-Dickinson Company, are equipped with mechanisms for deflecting (sorting) single cells into individual containers, such as the wells of an $8 \times 12$ (96 well) microculture plate. However, the typical cell staining procedure employed in a cell sorting experiment will not work for sorting low-frequency antigen-specific B cells. For example, for labeling B cells expressing antibodies specific for a hapten, a typical staining approach would be to conjugate the hapten to a carrier protein which is labeled with biotin and FITC-avidin. The labeled B cells are then stained with hasten-carrier protein-biotin and FITC-avidin. If the B cells with the desired antigen specificity occur at low frequencies, such as about $1 \times 10^{-5}$ among the IgG-expressing B cells, the B cells producing antibodies to the carrier protein, biotin, avidin, FITC or the cross-linkers used in conjugation will all show fluorescence, and there may be many more of these B cells than the antigen-specific B cells of interest.

In the present invention, the staining method employs two antigen probes with different fluorochromes linked to the antigens, preferably with different carriers and cross-linkers. For example, for labeling B cells expressing antibodies with a specificity to peptide A, the cells are labeled with peptide A-carrier protein P1-fluorochrome F1 and with peptide A-carrier protein P2-fluorochrome F2. The B cells that bind to peptide A, therefore, will display two colors which can be viewed in two of the FACS channels. In contrast, the B cells binding to P1, P2, F1, or F2 will display only one color, and can be viewed in only one of the FACS channels.

To solve the background noise problem which arises due to the fact that certain activated cells are autofluorescent or have sticky plasmamembranes, one designs one of the fluorescence channels to gate out such autofluorescent or sticky cells. This process is referred to as negative selection, and can be performed by one of two methods. In one method, the cells exhibiting positive fluorescence for a selected fluorochrome, such as F3, are excluded in the sorting, even though no probe is introduced. This negative selection procedure involves effectively sacrificing one of the fluorescence channels, i.e., the one which monitors F3, and selects out the cells which autofluorescence. This method has been used to reduce background noise to below $1 \times 10^{-5}$ in an FACS sorting procedure attempting to sort single allogeneic T cells from the spleens of mice, transplanted with allogenic T cells. Chang, J. -F. et al., *J. Immunol.* 147:851 (1991).

In another method, which can be combined with the first method, the mixture of cells are reacted with an F3 conjugated probe specific for a surface marker on an irrelevant population, such as CD3 on T cells. The cells exhibiting fluorescence for the F3 detector, either due to autofluorescence, stickiness, or positive specific reaction to the F3 probe, will all be excluded from sorting.

For increasing the specificity of sorting, additional fluorescent labels have been used on the B cells to be selected. These additional reagents label the surface γ chain, κ or λ chain, CD19, IgG, Ia, and Fc receptors which are expressed by B cells. By using fluorochromes that excite at different wavelengths, and by using one or two lasers, cells labeled with two, three, or four colors can be sorted.

Because the surface antigens γ chain, κ or λ chain, CD19, Ia, and Fc receptors are expressed by all B cells expressing IgG, the labeling of these additional surface molecules can help clear the nonspecific contamination of T cells, macrophages/monocytes, B cells expressing IgM, and other cells. However, these additional labels cannot enhance to any large extent the frequency of B cells expressing antibody to the desired antigen. The staining method of this invention includes the combination of the positive selection using multiple antigen probes that contain different fluorochromes and do not share the same carrier molecules and cross-linkers, and the negative selection which excludes cells which exhibit autofluorescence and membrane stickiness by gating out cells showing fluorescence in one of the selected fluorochrome windows.

In the present invention, the low frequency antigen-specific B cells are stained by reacting their antigen-specific receptors with two antigen probes, both comprising the specific antigen conjugated to one of two different protein carriers which are each labeled with a different fluorochrome. Different cross-linkers are also preferably used in each of the two antigen probes. Thus, the B cells that display two colors are not likely to bind to either of the carrier proteins, either of the fluorochromes, or either of the cross-linkers.

It is preferred if, in addition, these B cells are labeled with a fourth fluorochrome (F4) which stains surface γ chain, CD19, or surface κ chain, λ chain, Ia, or Fc receptors. With this additional label, the cells expressing three colors (for the positive selection) will most likely be the B cells expressing IgG specific to the antigen of interest.

C

Characterizing the relative antigen-binding affinities of antibodies on single cells.

The relative antigen-binding affinity of antibodies on B cells can be determined from the relative ratio of antigen labeling intensity to IgG labeling intensity. In the B cell antibody repertoire, theoretically a number of clones deriving from different germ line $V_H$ and $V_L$ and from different extents of somatic mutation can bind to the same antigenic molecule or even to the same antigenic epitope. When the number of sorted antigen-specific single B cells is more than what the single cell-PCR procedure can handle, those antigen-specific B cells expressing antibodies with higher affinity for the antigen should be selected for the single cell-PCR procedure, and the lower affinity ones should be rejected.

The relative antigen-binding affinity is determined from the relative extent of binding of antigen to the cells and of a targeting molecule which selects for IgG-producing B cells (preferably, an anti-IgG probe for surface IgG). To perform this calculation, a sub-job can be written into the computer program that processes the analysis and sorting during the FACS procedure. This sub-job will determine and express the intensity of fluorescence on each single cells being sorted in one of two different novel formats.

In the conventional format currently in use, the single cells being sorted are assigned identification numbers. For example, if cells are sorted into wells of an 8×12 (96 well) microculture plate, these single cells can be identified as A1, A2, A3 ... A12, B1, B2, B3 ... B12, H1, H2, H3 ... H12. In one novel modified sub-job format suitable for use with the methods of the invention, the intensity (channels) of fluorescence on each single cell being sorted is compiled into a table, based on the intensity of fluorescence. If fluorochrome #1 is used for labeling antigen, and fluorochrome #4 for labeling IgG, the ratio of fluorochrome #1 to fluorochrome #4 is also expressed. The table can then be used to determine which cells in which wells are best suited for PCR analysis.

In another format suitable for use with the invention, the individual single B cells (from the single wells) are plotted on a graph in which, for example, one axis represents the intensity of fluorephore #1 and the other axis represents the intensity of fluorephore #4. The individual B cells which have the highest level of intensity of fluorephore #1, and the lowest intensity level of fluorephore #4, have the highest antigen affinity, and are most suitable for PCR analysis and expression of their Fv fragments.

Example

Selecting single B cells specific for CD4 binding site on HIV-1 gp120 from infected individuals The murine monoclonal antibody G3-519, which recognizes a linear peptide epitope in the CD4-binding site of gp120 of HIV-1, has previously been disclosed. Sun, N. C. et al., *J Virol.* 63:3579 (1989) see also International application No. PCT/US90/07535; U.S. application Ser. No. 07/531,789 (incorporated by reference). G3-519 reacts with a broad-spectrum of HIV-1 laboratory strains and clinical isolates. In numerous fusion experiments using spleen cells of mice immunized with gp120, it has been found that this particular antigenic epitope is poorly immunogenic. It is relatively much more difficult to obtain hybrids secreting antibodies to this antigenic epitope than those secreting antibodies to other antigenic epitopes on gp120.

As described in PCT/US90/07535 and U.S. Ser. No. 07/531,789, G3-519 reacts with a synthetic peptide, I15P, corresponding to a segment in the CD4-binding domain of gp120. Using this peptide as the solid-phase antigen in ELISA, it has been found that the sera from HIV-1 infected individuals contain very low titers or undetectable levels of antibodies against I15P, again indicating that this particular antigenic epitope is weakly immunogenic in human beings.

It is reasonable to assume (based on the analysis set forth above) that because it is difficult to prepare hybrids from lymphocytes of mice that have been actively immunized with gp120, the frequency of the antigen-specific B cells, which produce antibody specific for CD4-binding site of gp120, probably occur at a frequency lower than $1 \times 10^{-5}$ among the IgG-bearing B cells of gp120 immunized mice. It is reasonable to extrapolate that the frequency of these B cells in HIV-1 infected individuals is probably also lower than $1 \times 10^{-5}$ among the IgG-bearing B cells.

Using the methods of the present invention, the mononuclear cells fraction is isolated by Ficoll/Hypaque density centrifugation of the heparinized peripheral blood from the HIV-1 infected donor. The T cells in the mononuclear cells are removed by resetting with sheep red blood cells and monocytes/macrophages are removed by adhering them to the substratum of plastic plates or to Sephadex-G10 beads. Hudson, L. and Hay, F. C., *Practical Immunology* (2nd. Ed. Blackwell Scientific Publications, Oxford, 1980). IgM-expressing B cells are removed by panning with a petri dish coated with affinity-purified goat IgG F(ab')$_2$ fragment which is specific for human IgM. Mage, M. G., *Current Protocols in Immunology*, Eds. Coligan, J. E. et al. (Wiley Interscience, New York 1991) §3.5.1. The remaining cells are enriched IgG-bearing B cells, which are still contaminated with some T cells, monocytes/macrophages, IgM-bearing B cells, and numerous other kinds of white cells.

A similar preparation of cells should also be prepared from a normal donor. These cells are to be reacted with the staining reagents, and used to set the gating thresholds for the FACS sorting.

Two fluorescence-labeled antigen probes are to be used. Peptide I15P is conjugated to two different fluorochromes. Alternatively, the peptide is conjugated to two carrier proteins, or molecules, which are each labeled with a different fluorochrome. The preferred antigen probes are:

I15P-FITC or I15P - ovalbumin - FITC

I15P-TR (Texas Red) or I15P - dextran - TR

Peptide I15P is an oligopeptide with 15 amino acid residues, none of which are cysteine residues. For the purposes of conjugation, a cysteine residue is added to the N-terminal or C-terminal end of I15P during the peptide synthesis, preferably using a typical automated peptide synthesizer, such as one from Applied Biosystems. The added cysteine residues provided the free SH groups at the termini of the peptides for cross-linking to the fluorochromes or to the carrier molecules. One may also add a few residues, such as glycine and serine residues, between the cysteine residue and the antigenic I15P peptides. The spacer minimizes stearic constraints introduced by the conjugation to the fluorochrome or the carrier protein.

The carrier molecules need not be proteins. However, proteins from various organisms probably provide a large number of possible carrier molecules. The preferred carrier molecules are those which are likely not to be antigenic in human serum. Suitable carrier molecules for use in the present invention are ovalbumin, a protein, and dextran, a polysaccharide.

A polysaccharide must be conjugated differently from a protein. Ovalbumin has a number of amino groups that can serve as the sites for cross-linking, whereas dextran molecules need to be modified to contain active groups for cross-linking. Dextran of molecular weight of 15,000-20,000 can be purchased from Sigma Chemical Co. (St. Louis, MO). The modification is adopted from Brunswick, M. et al. *J. Immunol.* 140:3364 (1988). Briefly, dextran is reacted with ethylenediamine dihydrochloride (Fluka, Ronkonkoma, N.Y.) to form AECM-dextran, which is then reacted with N-succinimidyl 3-iodoacetamido propionate (SIAP, from Aldrich Chemical Co., Milwaukee, WI) to form SIAP-dextran. This modified dextran can then coupled with the peptide with the free SH group to form the following product.

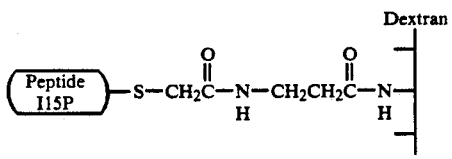

As discussed above, the cross-linkers for the peptide and ovalbumin are preferably different. A number of cross-linkers are available (for example, from Pierce Chemical Co., Rockford, IL) and are suitable for use in the invention. The choice and design of cross-linkers can also be made by referring to the handbook by Wong, S. S., *Chemistry of Protein Conjugation and Cross-Linking* (CRC Press, Boca Raton 1991). One preferred choice for cross-linking amino groups of ovalbumin and the sulfhydryl groups is 2,4,-dinitrophenyl-p-(β-nitrovinyl) benzoate. The structure of the coupled product is shown below.

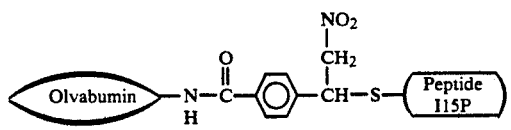

The third fluorochrome is to be sacrificed and is for excluding the autofluorescent or sticky cells. The preferred fluorochrome detector is the one for phycoerythrin (PE). In one embodiment, the mixture of cells need not be reacted with a probe labeled with PE. In the gating setting, the cells exhibiting positive fluorescence for PE are excluded (negative selection). The preferred embodiment for the present invention in that PE is conjugated to IgG.F(ab')2 of a murine monoclonal antibody specific for CD3.

MAHCD3.F(ab')2-PE

The fourth fluorochrome, for labeling surface γ chain, is an affinity purified goat IgG F(ab')2 fragment specific for human IgG(γ) that is labeled with allophycocyanin (APC):

GAHIG.F(ab')2-APC

An alternative for the fourth fluorochrome is for labeling surface CD19. The preferred reagent is the mouse monoclonal antibody IgG fragment F(ab')2, specific for human CD19, labeled APC:

MAHCD19.F(ab')2-APC

Purified F(ab')2 is used instead of whole IgG because deleting the Fc portion can avoid having the molecule bind to Fc receptors on the B cells or macrophages/monocytes. F(ab')2 preparations of goat-anti-human IgG and murine monoclonal antibody against human CD19 are available from various commercial sources. For example, goat IgG F(ab')2 anti-human IgG may be purchased from Chemicon International (Temecula, CA) and mouse monoclonal antibody IgG F(ab')2 anti-human CD19 may be purchased from Tago, Inc. (Burlingame, CA). Various fluorochromes that are already modified in various ways for conjugation are also available commercially, e.g. from Biomeda Corp. (Foster City, CA) and Molecular Probes, Inc. (Eugene, OR). The modified fluorochromes and properly modified antigens, such as I15P peptide, can be coupled to the activated carrier molecules at the same time.

The cell preparation enriched for B cells is incubated for 30 minutes at 40° C. with the mixture of the four probes directly conjugated with the fluorochromes. The incubation is performed in basic culture medium containing 1% fetal calf serum. All incubation and washing fluids are culture medium containing 1% fetal calf serum (to keep the cells healthy) to minimize nonspecific sticking of the protein probes to cells, and all procedures are performed at 4° C. to prevent capping and patching of the bound surface antigens.

The FACS sorting procedure is performed with a FACS Star Plus TM (Becton Dickinson) which has two lasers and is outfitted with an automated cloning accessory and can sort single cells into the wells of an 8×12 microculture plates. The setting of thresholds or windows for the forward light scattering, right-angle light scattering, and the four colors is performed with the cells from a normal donor. These cells are prepared and stained as with the experimental sample. The forward light scattering, which can distinguish the small-sized dead cells, and the right-angle light scattering, which can distinguish the high granularity of macrophages and granulocytes, are included in the gating to cut down noises from dead cells and granulocytes.

It should be understood that the examples, terms and expressions used herein are exemplary only and not limiting, and that the scope of the invention is defined only by the claims which follow, and includes all equivalents of the subject matter of the claims.

I claim:

1. A method of selecting antigen-specific B lymphocytes from a mixture of cells using a fluorescence activated cell sorting apparatus which has several channels, each of said channels capable of viewing a different fluorochrome, comprising:
    a) labeling B lymphocytes in the mixture with at least two different antigen probes, wherein each of said probes comprises an antigen which binds the antibodies on the target B lymphocyte surface, said antigen conjugated with a fluorochrome wherein said fluorochromes yield different colors upon activation;
    b) introducing an additional probe conjugated with an additional different fluorochrome, such probe being specific for cell populations which are not B lymphocytes wherein the additional fluorochrome adheres to and labels cells with a sticky cell membrane;
    c) selecting B lymphocytes which are positive for the fluorochromes attached to the antigen probes, but eliminating and not selecting those cells which are positive for the additional fluorochrome, or which display a fluorescence level greater than a specified level in the channel in which the additional fluorochrome is viewed.

2. The method of claim 1 wherein one antigen probe is labeled with FITC, the other antigen probe is labeled with Texas red, and the additional fluorochrome is phycoerythrin.

3. The method of claim 1 wherein three probes are used, each associated with a different fluorochrome, and further including labeling B lymphocytes with a targeting molecule specific for a marker unique to B lymphocytes, and wherein the targeting molecule is labeled with a fluorochrome yielding a color different from those of the antigen probes and additional probe.

4. The method of claim 3 wherein the targeting molecule is F(ab')2 specific for IgG.

5. The method of claim 3 wherein the marker is the surface IgG, κ and λ chains, CD19, Ia, or Fc receptors which are expressed by B lymphocytes.

6. The method of claim 3 wherein the fluorochrome which the targeting molecule is labeled with is allophycocyanin.

7. The method of claim 1 wherein, in the antigen probes, a carrier molecule is conjugated between the antigens and the fluorochromes.

8. The method of claim 7 wherein a different carrier molecule is associated with each antigen probe.

9. The method of claim 8 wherein one carrier molecule is ovalbumin and the other is dextran.

10. The method of claim 1 wherein the fluorescence activated cell sorting is performed with a fluorescence activated cell sorting apparatus, which can sort individual cells into wells of 8×12 well microculture plates.

11. The method of claim 10 wherein the quantity of fluorochrome on each individual B lymphocyte is determined from the intensity of color from the fluorochrome, and this value is used to determine which cells should be separated from the B lymphocyte population.

12. The method of claim 10 wherein for each B lymphocyte, the ratio of the quantity of fluorochrome from one of the antigen probes over the quantity of fluorochrome from the B lymphocyte marker is determined.

13. The method of claim 12 wherein the B lymphocytes with the highest of said ratio are determined to have the highest affinity for the antigen.

14. The method of claim 10 further amplifying by PCR the $V_H$ and $V_L$ gene segments of the labeled B lymphocytes which were sorted from the B lymphocytes population.

15. The method of claim 1 further including the step of amplifying by PCR the $V_H$ and $V_L$ nucleotide sequences of the B lymphocytes which are selected.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
    ( A ) LENGTH: 15 nucleotides
    ( B ) TYPE: nucleic acid
    ( C ) STRANDEDNESS: Single stranded
    ( D ) TOPOLOGY: Linear ( x i ) SEQUENCE DESCRIPTION: SEQ ID NO:1:

GAGGTGCAGC TGGTG 15

( 2 ) INFORMATION FOR SEQ ID NO:2:

( i ) SEQUENCE CHARACTERISTICS:
        ( A ) LENGTH: 15 nucleotides
        ( B ) TYPE: nucleic acid
        ( C ) STRANDEDNESS: Single stranded
        ( D ) TOPOLOGY: Linear ( x i ) SEQUENCE DESCRIPTION: SEQ ID NO:2:

GAGATGCAAC TGGTG 15

( 2 ) INFORMATION FOR SEQ ID NO:3:

( i ) SEQUENCE CHARACTERISTICS:
        ( A ) LENGTH: 15 nucleotides
        ( B ) TYPE: nucleic acid
        ( C ) STRANDEDNESS: Single stranded
        ( D ) TOPOLOGY: Linear ( x i ) SEQUENCE DESCRIPTION: SEQ ID NO:3:

GAGGTACATT TGGTG 15

( 2 ) INFORMATION FOR SEQ ID NO:4:

( i ) SEQUENCE CHARACTERISTICS:
        ( A ) LENGTH: 15 nucleotides
        ( B ) TYPE: nucleic acid
        ( C ) STRANDEDNESS: Single stranded
        ( D ) TOPOLOGY: Linear ( x i ) SEQUENCE DESCRIPTION: SEQ ID NO:4:

CAGGTGCAAC TACAG 15

( 2 ) INFORMATION FOR SEQ ID NO:5:

( i ) SEQUENCE CHARACTERISTICS:
        ( A ) LENGTH: 15 nucleotides
        ( B ) TYPE: nucleic acid
        ( C ) STRANDEDNESS: Single stranded
        ( D ) TOPOLOGY: Linear ( x i ) SEQUENCE DESCRIPTION: SEQ ID NO:5:

CAGATCAACT TAAAG 15

( 2 ) INFORMATION FOR SEQ ID NO:6:

( i ) SEQUENCE CHARACTERISTICS:
        ( A ) LENGTH: 15 nucleotides
        ( B ) TYPE: nucleic acid
        ( C ) STRANDEDNESS: Single stranded
        ( D ) TOPOLOGY: Linear ( x i ) SEQUENCE DESCRIPTION: SEQ ID NO:6:

CAGGTGCAGC TGCCG 15

( 2 ) INFORMATION FOR SEQ ID NO:7:

( i ) SEQUENCE CHARACTERISTICS:
        ( A ) LENGTH: 15 nucleotides
        ( B ) TYPE: nucleic acid
        ( C ) STRANDEDNESS: Single stranded (D) TOPOLOGY: Linear (xi) SEQUENCE DESCRIPTION: SEQ ID NO:7:

GACATCCAGA TGACC 15

(2) INFORMATION FOR SEQ ID NO:8:

(i) SEQUENCE CHARACTERISTICS:
        (A) LENGTH: 15 nucleotides
        (B) TYPE: nucleic acid
        (C) STRANDEDNESS: Single stranded
        (D) TOPOLOGY: Linear (xi) SEQUENCE DESCRIPTION: SEQ ID NO:8:

GATATTGTGA TGACT 15

(2) INFORMATION FOR SEQ ID NO:9:

(i) SEQUENCE CHARACTERISTICS:
        (A) LENGTH: 15 nucleotides
        (B) TYPE: nucleic acid
        (C) STRANDEDNESS: Single stranded
        (D) TOPOLOGY: Linear (xi) SEQUENCE DESCRIPTION: SEQ ID NO:9:

GACATCGTGA TGACC 15

(2) INFORMATION FOR SEQ ID NO:10:

(i) SEQUENCE CHARACTERISTICS:
        (A) LENGTH: 15 nucleotides
        (B) TYPE: nucleic acid
        (C) STRANDEDNESS: Single stranded
        (D) TOPOLOGY: Linear (xi) SEQUENCE DESCRIPTION: SEQ ID NO:10:

GAAATTGTAT TGACA 15

(2) INFORMATION FOR SEQ ID NO:11:

(i) SEQUENCE CHARACTERISTICS:
        (A) LENGTH: 15 nucleotides
        (B) TYPE: nucleic acid
        (C) STRANDEDNESS: Single stranded
        (D) TOPOLOGY: Linear (xi) SEQUENCE DESCRIPTION: SEQ ID NO:11:

GAAATTGTGT TGACG 15

(2) INFORMATION FOR SEQ ID NO:12:

(i) SEQUENCE CHARACTERISTICS:
        (A) LENGTH: 15 nucleotides
        (B) TYPE: nucleic acid
        (C) STRANDEDNESS: Single stranded
        (D) TOPOLOGY: Linear (xi) SEQUENCE DESCRIPTION: SEQ ID NO:12:

GAAATACTGA TGACG 15

(2) INFORMATION FOR SEQ ID NO:13:

(i) SEQUENCE CHARACTERISTICS:
        (A) LENGTH: 29 nucleotides
        (B) TYPE: nucleic acid
        (C) STRANDEDNESS: Single stranded
        (D) TOPOLOGY: Linear (xi) SEQUENCE DESCRIPTION: SEQ ID NO:13:

-continued

GAAGTAGTCC TTGACCAGGC AGCCCAGGG 29

( 2 ) INFORMATION FOR SEQ ID NO:14:

( i ) SEQUENCE CHARACTERISTICS:
        ( A ) LENGTH: 27 nucleotides
        ( B ) TYPE: nucleic acid
        ( C ) STRANDEDNESS: Single stranded
        ( D ) TOPOLOGY: Linear ( x i ) SEQUENCE DESCRIPTION: SEQ ID NO:14:

CCAAGCTTGG AGCAGGGCGC CAGGGGG 27

( 2 ) INFORMATION FOR SEQ ID NO:15:

( i ) SEQUENCE CHARACTERISTICS:
        ( A ) LENGTH: 22 nucleotides
        ( B ) TYPE: nucleic acid
        ( C ) STRANDEDNESS: Single stranded
        ( D ) TOPOLOGY: Linear ( x i ) SEQUENCE DESCRIPTION: SEQ ID NO:15:

GGCAGTTCCA GATTTCAACT GC 22

( 2 ) INFORMATION FOR SEQ ID NO:16:

( i ) SEQUENCE CHARACTERISTICS:
        ( A ) LENGTH: 26 nucleotides
        ( B ) TYPE: nucleic acid
        ( C ) STRANDEDNESS: Single stranded
        ( D ) TOPOLOGY: Linear ( x i ) SEQUENCE DESCRIPTION: SEQ ID NO:16:

CCAAGCTTCA TCAGATGGCG GGAGAT 26